US010835519B2

(12) United States Patent
Plas et al.

(10) Patent No.: US 10,835,519 B2
(45) Date of Patent: Nov. 17, 2020

(54) TARGETING METABOLIC ADAPTIVE RESPONSES TO CHEMOTHERAPY

(71) Applicant: University of Cincinnati, Cincinnati, OH (US)

(72) Inventors: David Plas, Cincinnati, OH (US); Catherine Behrmann, Fairfield, OH (US)

(73) Assignee: University of Cincinnati, Cincinnati, OH (US)

(*) Notice: Subject to any disclaimer, the term of this patent is extended or adjusted under 35 U.S.C. 154(b) by 0 days.

(21) Appl. No.: 15/851,891

(22) Filed: Dec. 22, 2017

(65) Prior Publication Data
US 2018/0117015 A1 May 3, 2018

Related U.S. Application Data

(60) Division of application No. 15/019,265, filed on Feb. 9, 2016, which is a continuation-in-part of application No. 13/761,765, filed on Feb. 7, 2013.

(60) Provisional application No. 61/596,258, filed on Feb. 8, 2012.

(51) Int. Cl.
*A61K 31/436* (2006.01)
*A61K 31/381* (2006.01)
*A61K 31/421* (2006.01)
*A61K 45/06* (2006.01)

(52) U.S. Cl.
CPC .......... *A61K 31/436* (2013.01); *A61K 31/381* (2013.01); *A61K 31/421* (2013.01); *A61K 45/06* (2013.01)

(58) Field of Classification Search
CPC ... A61K 31/436; A61K 31/381; A61K 31/421
See application file for complete search history.

(56) References Cited

U.S. PATENT DOCUMENTS

2006/0094674 A1* 5/2006 Neel ............... A61K 31/436
514/44 A
2015/0018411 A1 1/2015 Diederich et al.

FOREIGN PATENT DOCUMENTS

WO 20120168345 12/2012

OTHER PUBLICATIONS

Li et al., Oncology Report, 2012;27:461-466.*
Campbell et al., New England Journal of Medicine, 2006;355:2452-66.*
Recher et al, Blood, 2005; 105(6): 2527-2534.
(Continued)

*Primary Examiner* — San Ming R Hui
(74) *Attorney, Agent, or Firm* — Dinsmore & Shohl LLP

(57) ABSTRACT

Methods for targeting adaptive responses to chemotherapy are described. In various embodiments, a method comprises administering at least one compound that inhibits S6K1, mTORC1 or upstream or downstream pathway components of S6K1 or mTORC1, in association with administration of at least one inhibitor of PPARα, PPARδ, or PGC1α. In various embodiments, the compound that inhibits S6K1, mTORC1, or upstream or downstream pathway components of S6K1 or mTORC1 is rapamycin, everolimus, temsirolimus, or imatinib. The inhibitor of PPARα, PPARδ, or PGC1α can be an antagonist or an inverse agonist selected from GW6471, GSK3787, GSK0660, and ST247.

10 Claims, 13 Drawing Sheets

(56) References Cited

OTHER PUBLICATIONS

Hsu et al, Cancer cell metabolism: Warburg and beyond. Cell 2008; 134: 703-707.
Plas et al, Akt and Bcl-xL Promote Group Factor-Independent Survival through Distinct Effects on Mitochondrial Physiology, J Biol Chem 2001; 276: 12041-8.
Rathmell et al, Akt-directed glucose metabolism an prevent Bax conformation change and promote growth factor-Independent survival. Mol Cell Biol 2003; 23: 7315-28.
Buzzai et al, The glucose dependence of Akt-transformed cells can be reversed by pharmacologic activation of fatty acid beta-oxidation. Oncogene 2005; 24: 4165-73.
Schafer et al, Antioxidant and oncogene rescue of metabolic defects caused by loss of matrix attachment. Nature 2009; 461: 109-13.
Wise et al, Myc regulates a transcriptional program that stimulates mitochondrial glutaminolysis and leads to glutamine addiction. Proc Natl Acad Sci USA 2008; 105: 18782-7.
Bonnet et al, A mitochondrial-K+ channel axis is suppressed in cancer and its normalization promotes apoptosis and inhibits cancer growth, Cancer Cell 2007; 11: 37-51.
Vander Heiden MG; Targeting cell metabolism in cancer patients; Sci Transi Med 2010; 2: 31ed1.
Pelicano et al, Glycolysis inhibition for anticancer treatment. Oncogene 2006; 25: 4633-46.
Mason et al, Aerobic Glycolysis suppresses p53 activity to provide selective protection from apoptosis upon loss of growth signals or inhibition of BCR-Abl. Cancer Res 2010; 70: 8066-76.
Gottschalk et al, Imatinib (STI751)-mediated changes in glucose metabolism in human leukemia BCR-ABL-positive cells. Clin Cancer Res 2004; 10: 6661-8.
Barnes et al, Chronic myeloid Leukemia: an investigation into the role of Bcr-Abl-induced abnormalities in glucose transport regulation. Oncogene 2005; 24: 3257-67.
Klawitter et al, Metabolic characteristics of imatinib resistance in chronic myeloid leukemia cells. Br J Pharmacol 2009; 158: 588-600.
Kominsky, et al, Abnormalities in glucose uptake and metabolism in imatinib-resistance human BCR-ABL-positive cells, Clin Cancer Res 2009; 15: 3442-50.
Druker et al, Five-year follow up of patients receiving imatinib for chronic myeloid leukemia, N Engl J Med 2006; 355: 2408-17.
Branford et al, High frequency of point mutations clustered within the adenosine triphosphate-binding region of BCR/ABL in patients with chronic myeloid leukemia or pH-positive acute lymphoblastic leukemia who develop imatinib (STI571) resistance; Blod 2002; 99: 3472-5.
Burchert et al, Compensatory P13-kinase/AktmTor activation regulates imatinib resistance development; Leukemia 2005; 19: 1774-82.
Hochhaus et al, Molecular and chromosomal mechanisms of resistance to imatinib (STI571) therapy; Leukemia 2002; 16: 2190-6.
Mccubbrey et al, Targeting survival cascades induced by activation of Ras/Raf/MEK/ERK, P13K/PTEN/Akt/mTOR and Jak/STAT pathways for effective leukemia therapy; Leukemia 2008; 22: 708-22.
Skorski et al, Transformation of hematopoietic cells by BCR/ABL requires activation of a PI-3k?Akt-dependent pathway; EMBO J 1997; 16: 6151-61.
Tandon et al, Requirement for ribosomal protein S6 kinase 1 to mediate glycolysis and apoptosis resistance induced by Pten deficiency; Proc Natl Aced Sci USA 2011; 108: 2361-5.
Thoreen et al, An ATP-competitive Mammalian Target of Rapamycin Inhibitor Reeals Rapamysin-Resistant Functions of mTORC1; J Biol Chem 2009/ 284: 8023-32.
Markova et al, Novel pathway in Bcr-Abl signal transduction involves Akt-independent, PLC-gamma1-drive activation of mTOR/P70S6-kinase pathway; Oncogene 2010; 29:739-51.
Vander Heiden et al, Growth Factors can influence cell growth and survival through effects on glucose metabolism; Mol Cell Biol 2001; 21: 5899-912.
Lum et al, Growth factor regulation of autophagy and cell survival in the absence of apoptosis; Cell 2005; 120: 237-48.
Inoki et al, TSC2 mediates cellular energy response to control cell growth and survival; Cell 2003; 115: 577-90.
Kim et al, Regulation of TORC1 by Rag GTPases in nutrient response; Nat Cell Biol 2008; 10: 935-45.
Nobukuni et al, Amino acids mediate mTOR/raptor signaling through activation of class 3 phosphatidylinositol 3OH-kinase; Proc Natl Acad Sci USA 2005; 102: 14238-43.
Sancak et al, The Rag GTPases bind raptor and meidate amino acid signaling to mTORC1; Science 2008; 320: 1496-501.
O'Reilly et al, mTOR inhibition induces upstream receptor tyrosine kinase signaling and activates Akt; Cancer Res 2006; 66: 1500-8.
Sarbassov et al, Prolonged rapamycin treatment inhibits mTORC2 assembly nad Akt/PKB; Mol Cell 2006; 22: 159-68.
Nardella et al, Differential expression of S6K2 dictates tissue-specific requirement for S6K1 in mediating aberrant mTORC1 signaling and tumorigenesis; Cancer Res 2011; 71: 3669-75.
Kharas et al, Ablation ofP13K blocks BCR-ABL leukemogenesis in mice, and a dual P13K/mTOR inhibitor prevents expansion of human BCR-ABL + Leukemia Cells; J Clin Invest 2008; 118: 3038-50.
Mohi et al, Combination of rapamycin and protein tyrosine kinase (PTK) inhibitors for the treatment of keukemias caused by ondogenic PTKs; Proc Natl Acad Sci USA 2004; 101: 3130-5.
Choo et al, Glucose addiction of TSC null cells is caused by failed mTORC1-dependent balancing of metabolic demand with supply; Mol Cell 2010; 38: 487-99.
Eaton et al, Mammalian mitochondrial beta-oxidation; Biochem J 1996; 320 (Pt 2): 345-57.
Bonnefont et al, Camitine palmitoyltransferases 1 and 2: biochemical, molecular, and medical aspects; Mol Aspects Med 2004; 25: 495-520.
Zaugg et al, Camitine Palmitoyltransferase 1C promotes cell survival and tumor growth under conditions of metabolic stress; Genes Dev 2011; 25: 1041-51.
Chahoub et al, PTEN and the PI3-kinase pathway in cancer; Annu Rev Pathol 2009; 4: 127-50.
Duvel et al, Activation of a Metabolic Gene Regulatory Network Downstream of mTORComplex 1; Mol Cell 2010; 39: 171-83.
Chalhoub et al, S6k1 is not required for Pten-deficient neuronal hypertrophy; Brain Res 2006; 1100: 32-41.
Dowling et al, mTORC1-mediated cell proliferation, but not cell growth, controlled by the 4E-BPs; Science 2010; 328: 1172-6.
Um et al, Nutrient overload, insulin resistance, and ribosomal protein S6 kinase 1, S6K1; Cell Metab 2006; 3: 393-402.
Ito et al, PML Targeting eradicates quiescent leukemia-initiating cells; Nature 2008; 453: 1072-8.
Plas et al, Tubers and tumors: rapamycin therapy for benign and malignant tumors; Curr Opin Cell Biol 2009; 21: 230-6.
Sengupta et al, mTORC1 controls fasting-induced ketogenesis and its modulation by aging; Nature 2010; 468: 1100-4.
Um et al, Absence of S6K1 protects against age- and diet-induced obesity while enhancing insulin sensitivity; Nature 2004; 431: 200-5.
Serra et al, PI3K inhibition results in enhanced HER signaling and acquired ERK dependency in HER2-overexpressing breast cancer; Oncogene 2011; 30: 2547-57.
Djouadi et al, Characterization of fatty acid oxidatin in human muscle mitochondria and myoblasts; Mol Genet Metab 2003; 78: 112-8.
Shima et al, Disruption of the p70(s6k)/p85(s6k) gene reveals a small mouse phenotypeand a new functional S6 kinase; EMBO J 1998; 17: 6649-59.

\* cited by examiner

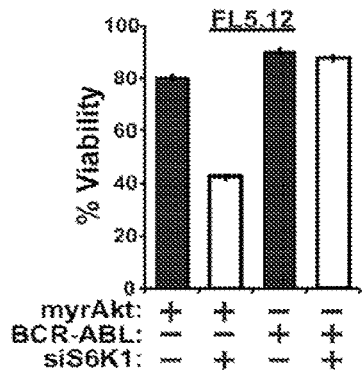 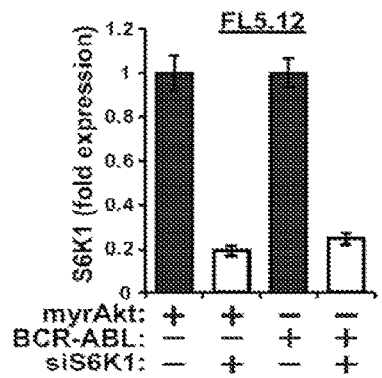 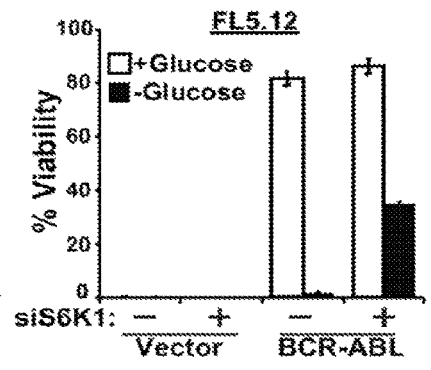
FIG. 4A            FIG. 4B            FIG. 4C
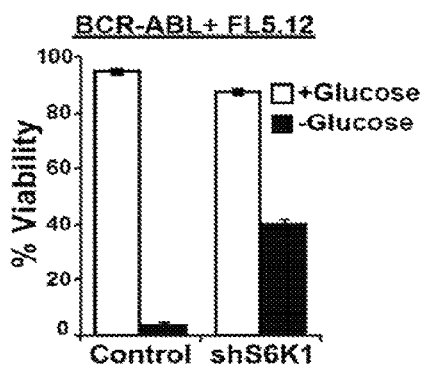 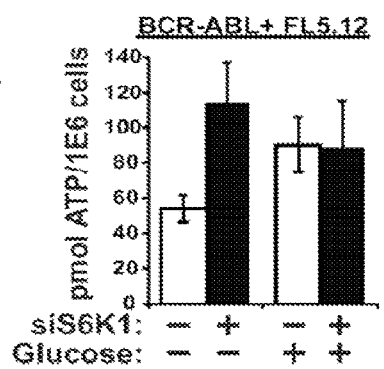 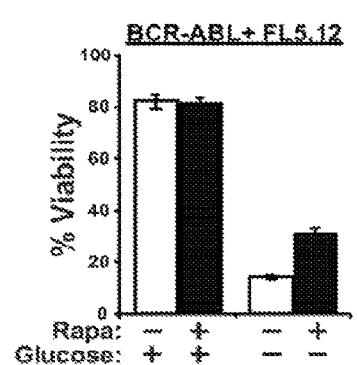
FIG. 4D            FIG. 4E            FIG. 4F
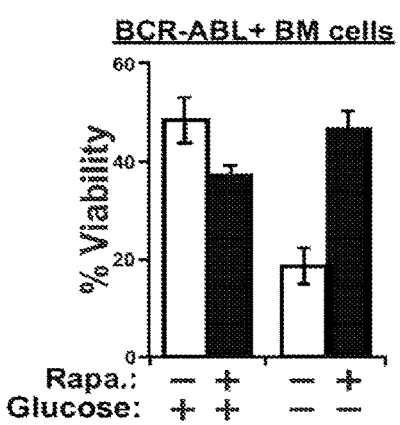 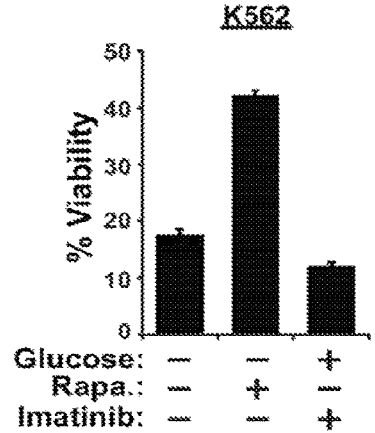
FIG. 4G            FIG. 4H

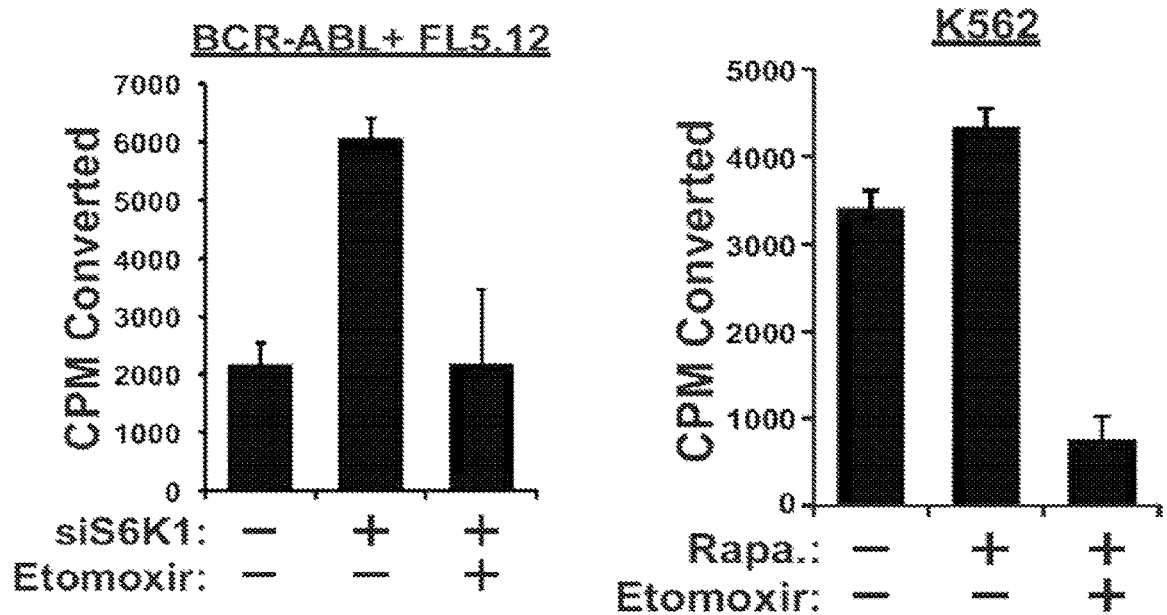
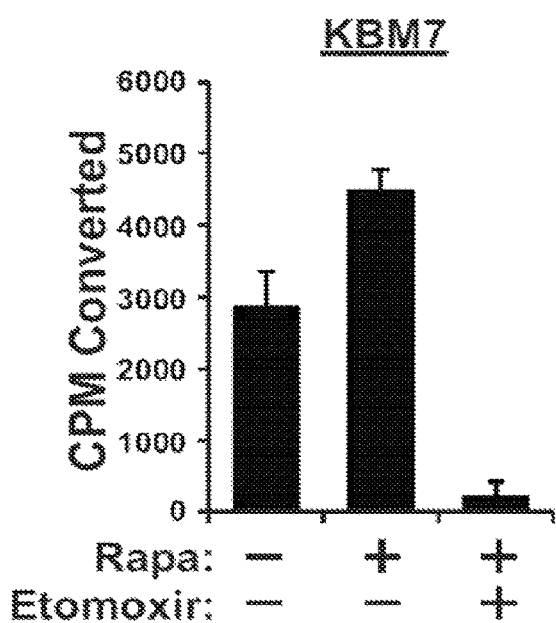 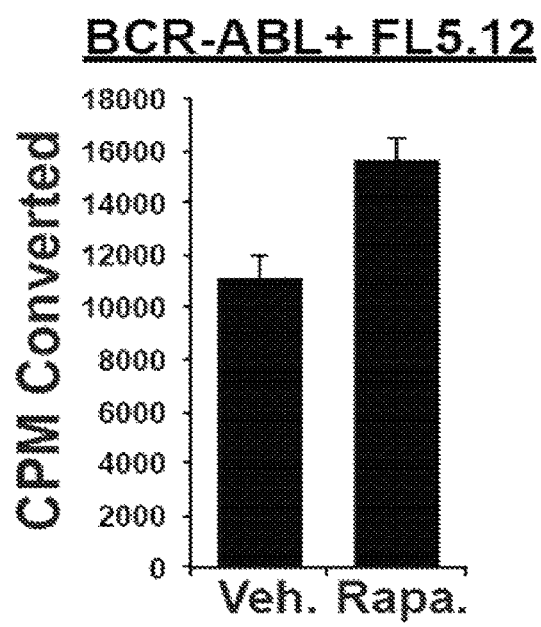
FIG. 7A
FIG. 7B
FIG. 7C
FIG. 7D

TARGETING METABOLIC ADAPTIVE RESPONSES TO CHEMOTHERAPY

CROSS-REFERENCE TO RELATED APPLICATIONS

This application is a divisional of U.S. application Ser. No. 15/019,265, filed Feb. 9, 2016, which is a continuation-in-part of U.S. application Ser. No. 13/761,765, filed Feb. 7, 2013, which claims priority under 35 U.S.C. § 119(e) to U.S. Provisional Application Ser. No. 61/596,258, filed Feb. 8, 2012, titled "Targeting Metabolic Adaptive Responses to Chemotherapy," each of which is incorporated by reference in its entirety.

GOVERNMENT INTERESTS

This invention was developed, at least in part, made with Government support under CA133164 and CA168815 awarded by the National Institutes of Health. The Government has certain rights in the invention.

BACKGROUND

One of the most common types of leukemia is chronic myelogenous leukemia (CML). CML accounts for approximately 10% of adult leukemia. In most cases of CML, the disorder is triggered by expression of the BCR-ABL oncogene from a translocation between one chromosome 9 and one chromosome 22 that results in a Philadelphia chromosome. The Philadelphia chromosome contains a fused BCR-ABL gene which produces an abnormal protein that activates constitutively a number of cell activities that promote cell growth. In particular, BCR-ABL drives apoptosis resistance in leukemic cells by activating the phosphatidylinositol 3'-kinase (PI3K)/Akt pathway. The Akt signaling pathway can trigger increased cell survival and cell growth, and consequently, an increased cellular metabolism that is glucose-dependent. While current treatments for CML and other cancers, such as treatment with rapamycin, can decrease or even suppress glycolysis through inactivation of the downstream protein kinase S6K1, these treatments do not result in the expected level of apoptosis. In some instances, the cancer cells may even develop a resistance to the treatment and cause relapse.

SUMMARY

Methods for targeting adaptive responses to chemotherapy are described. In various embodiments, a method comprises administering at least one compound that inhibits S6K1, mTOR, mTORC1, or upstream or downstream pathway components of S6K1 or mTORC1, in association with administration of at least one inhibitor of PPARα, PPARδ, or PGC1α.

In various embodiments, a method of treating cancer in a subject includes administering a compound that inhibits at least one component of the mTORC1-S6K1 pathway in association with administration of an inhibitor of PPARα, PPARδ, or PGC1α.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE DRAWINGS

The detailed description is described with reference to the accompanying figures.

FIG. 4A illustrates the viability of BCR-ABL$^+$ FL5.12 cells and myrAkt-expressing FL5.12 cells upon loss of S6K1.

FIG. 4B illustrates the efficacy of S6K1 knockdown in the treatments illustrated in FIG. 4A.

FIG. 4C illustrates the increased survival rate of BCR-ABL$^+$ cells when cultured in 0.2 mM glucose media when S6K1 is targeted with siS6K1.

FIG. 4D illustrates the increased survival rate of BCR-ABL$^+$ cells when cultured in 0.2 mM glucose media when S6K1 is targeted with ShS6K1.

FIG. 4E illustrates increased ATP concentrations in S6K1-knockdown BCR-ABL$^+$ FL5.12 cells cultured in 0.2 mM glucose media.

FIG. 4F illustrates the survival advantage of BCR-ABL$^+$ FL5.12 in 0.2 mM glucose media in response to rapamycin-inactivation of S6K1.

FIG. 4G illustrates the survival advantage of BCR-ABL$^+$ primary murine bone marrow cells in 0.2 mM glucose media in response to rapamycin-inactivation of S6K1.

FIG. 4H illustrates the survival advantage of BCR-ABL$^+$ K562 cells in 0.2 mM glucose media in response to rapamycin-inactivation of S6K1.

FIG. 7A illustrates the effect of etomoxir on fatty acid oxidation in BCR-ABL$^+$ FL5.12 cells upon S6K1 inactivation.

FIG. 7B illustrates the effect of etomoxir and/or rapamycin on fatty acid oxidation in BCR-ABL$^+$ K562 cells.

FIG. 7C illustrates the effect of etomoxir and/or rapamycin on fatty acid oxidation in BCR-ABL$^+$ KBM7 cells.

FIG. 7D illustrates the induction of fatty acid oxidation by rapamycin in BCR-ABL$^+$ FL5.12 cells.

Figure 1A:
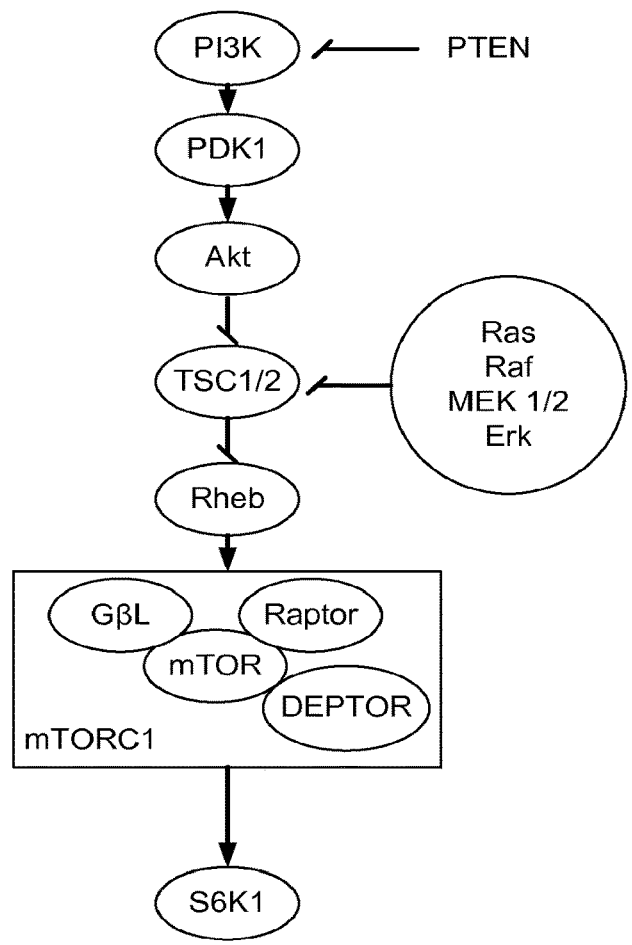
FIG. 1A is an illustration of the mTORC1-S6K1 pathway including upstream and downstream elements.

The embodiments set forth in the drawings are illustrative in nature and are not intended to be limiting of the embodiments as defined by the claims. Moreover, individual features of the drawings and the embodiments will be more fully apparent and understood in view of the detailed description.

DETAILED DESCRIPTION

Overview

Methods for targeting adaptive responses to chemotherapy are described. In particular, methods for treating cancer by administering a compound that inhibits at least one component of the mTOR pathway in association with administration of an inhibitor of PPARα, PPARδ, or PGC1α are described.

In the following discussion, general considerations are presented regarding methods for targeting adaptive responses to chemotherapy described herein. Next, administration of various compounds for targeting adaptive responses to chemotherapy is described. Finally, examples are described which illustrate particular embodiments. Consequently, performance of the example procedures is not limited to the example environment and the example environment is not limited to performance of the example procedures.

General Considerations

Chemotherapeutics that target cancer cell metabolism can enable long-term suppression of disease for patients since oncogenic signaling pathways, such as Ras, Akt, and Myc, reprogram the metabolism of transformed cells in order to promote cell survival. See, e.g., Hsu, et al., (2008) Cell 134: 703-7. In CML, the BCR-ABL oncogene activates glucose metabolism ("glycolysis") as part of its transforming activity. Increased glycolysis coupled with a requirement for cell survival is associated with loss-of-function mutations in the PTEN tumor suppressor, or activating mutations in PI3K subunits in multiple cancers. These mutations can trigger increased signaling through key downstream protein kinases, including Akt, mTORC1, and S6K1, which mediate increased glycolysis.

Activation of glycolysis in BCR-ABL$^+$ cells is associated with an increase in GLUT-1 glucose transporter molecules at the membrane. BCR-ABL inhibitors, such as imatinib, can cause a reduction in the surface localization of GLUT-1, which can correlate with decreased glucose uptake and lactate production. See, e.g., Klawitter et al., (2009) Br J Pharmacol 158: 588-600; and Kominsky et al., (2009) Clin Cancer Res 15:3442-50. Resistance to BCR-ABL inhibitors is observed in patients with advanced-stage CML, and can result from mutations in the BCR-ABL kinase domain, gene amplification, or activation of alternative signaling pathways. One such alternative signaling pathway is the mTORC1-S6K1 pathway including upstream and downstream elements. See, e.g., Druker et al., (2006) N Engl J Med 355:2408-17; Burchert et al., (2005) Leukemia 19: 1774-82; and Hochhaus et al., (2002) Leukemia 16: 2190-6.

The mTORC1-S6K1 pathway activates glycolysis and is important for the survival of transformed BCR-ABL$^+$ leukemia cells. See, e.g., McCubrey et al., (2008) Leukemia 22:708-22 and Skorski et al., (1997) EMBO J 16:6151-61. S6K1, a protein kinase, may be critical to oncogene-induced glycolysis in cancer cells. Therefore, inactivation of S6K1 or other components in the mTORC1-S6K1 pathway, including upstream and downstream elements, can reduce or suppress glycolysis in such cells. The mTORC1-S6K1 signaling pathway is illustrated in FIG. 1A.

Figure 1B:
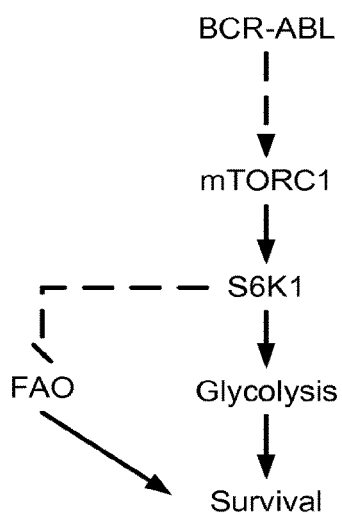
FIG. 1B illustrates the glucose-dependent survival mechanism that is activated by mTORC1-S6K 1.
Figure 1C:
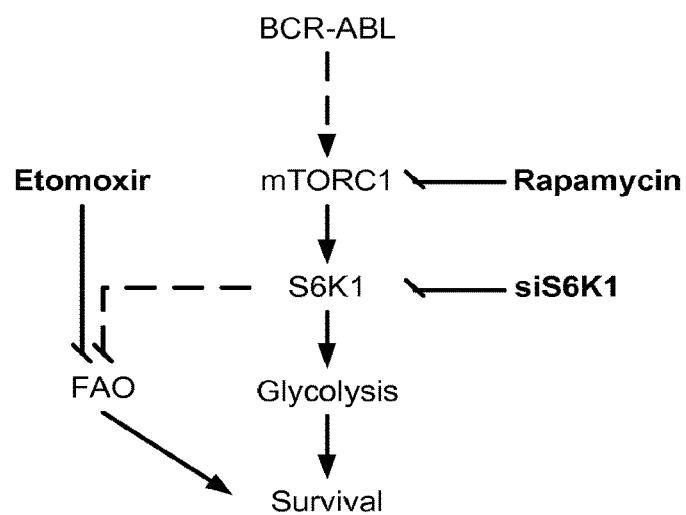
FIG. 1C illustrates coordinated inactivation of metabolic programs that negate BCR-ABL-dependent survival in accordance with one or more embodiments.

Although S6K1 is required for BCR-ABL to induce glycolysis, the metabolic requirements for survival can be altered when S6K1 is inactivated, as shown in FIG. 1B-1C. Rapamycin, an inhibitor of "mechanistic target of rapamycin" (mTOR), can inhibit the activation of S6K1, causing suppression of glycolysis. However, rapamycin produces a lower-than-expected level of cytotoxicity. In other words, though the rapamycin suppresses glycolysis, the cancer cells do not undergo apoptosis. For example, under low glucose conditions, S6K1 inactivation can confer a survival advantage to BCR-ABL$^+$ cells, and rapamycin treatment can recapitulate this advantage. Thus, an alternative metabolic program can compensate for the loss of S6K1 and provide a cell survival advantage.

In bone marrow transplant experiments using BCR-ABL$^+$ S6K1$^{-/-}$ cells, the oncogenic potential of BCR-ABL was not compromised, and trended towards more aggressive disease. This indicated that the oncogene can function independent of the mTORC1-S6K1 pathway that is required for BCR-ABL to induce glycolysis. Because the outcome differed from the delay in leukemia observed in PTEN-deficient S6K1$^{-/-}$ leukemias but was consistent with the lack of requirement for S6K1 in mediating neuronal hypertrophy, the requirement for S6K1 in oncogenesis may vary depending on the transforming mutations and cellular background.

In contrast to S6K1 inactivation, rapamycin can delay leukemia progression in mice transplanted with BCR-ABL$^+$ bone marrow cells. This difference may be related to the potential for rapamycin to reduce mTORC1 phosphorylation of additional targets that regulate cell cycle progression. Such targets can include, for example, 4EBP-1, S6K2, and ULK1. The target 4EBP1 mediates cytostatic responses, while S6K1 regulates growth and metabolism. Accordingly, rapamycin can have mixed effects in BCR-ABL$^+$ leukemogenesis, inducing a cytostatic response while activating S6K1-independent metabolic and survival effects. Thus, rapamycin can preserve BCL-ABL$^+$ leukemia-initiating cells, consistent with cytostatic and pro-survival effects of rapamycin and its analogs in solid tumor settings.

In some instances, decreased S6K1 levels can cause an increase in fatty acid metabolism or fatty acid oxidation (FAO). The increase in fatty acid metabolism can support glucose-independent survival of the cells when glycolysis is decreased.

FAO can be inversely correlated with signal transduction through the mTORC1-S6K1 pathway. However, because inactivation of mTORC1-S6K1 reduces glycolysis and induces programmed cell death in PTEN-deficient cells, increased FAO is not a necessary response to inactivation of mTORC1-S6K1. Thus, oncogene or cell-type specific factors may govern the metabolic response to mTORC1-S6K1 inactivation.

The decreased cytotoxic effect observed in clinical trials with rapamycin and its analogs suggest that feedback loops in the signal transduction pathways can induce compensatory survival signals Inhibitors that target one or more small molecules involved in the mTORC1-S6K1 pathway, including upstream and downstream elements, can be used to overcome feedback effects in signal transduction. In addition, metabolic adaptive responses can play a role in suppressing chemotherapy cytotoxicity. Accordingly, targeting such compensatory metabolic programs that contribute to cell survival can increase the therapeutic potential of agents that target the mTORC1-S6K1 pathway.

In various embodiments, combination of a FAO inhibitor with an inhibitor of a component of the mTORC1-S6K1 pathway, such as rapamycin, can result in an additive or synergistic cytotoxic effect. In particular, inhibitors of the peroxisome proliferator activated receptor α (PPARα), peroxisome proliferator activated receptor δ (PPARδ), or PPAR gamma coactivator 1α (PGC1α) in combination with an inhibitor of a component of the mTORC1-S6K1 pathway can result in increased cytotoxicity. In some embodiments, the inhibitors of PPARα, PPAR δ, or PGC1α could tip responses to inactivation of mTORC1-S6K1 towards induction of programmed cell death, as illustrated in FIG. 1C.

Therefore, in various embodiments, a method of treating cancer in a subject includes administering a compound that inhibits a component of the S6K1, mTOR, mTORC1, or upstream or downstream pathway components of S6K1 or mTORC1 mTORC1-S6K1 pathway in association with administration a compound that inhibits PPARα, PPARδ, or PGC1α. The compound that inhibits a component of the mTORC1-S6K1 pathway can be rapamycin or a rapalog, everolimus, temsirolimus, Torin1, BEZ235, other similar or equivalent compounds, or combinations thereof. The target of the compound can be, for example, S6K1, mTOR, mTORC1, or upstream or downstream pathway components of S6K1 or mTORC1. In various embodiments, the inhibitor is an antagonist of PPARα, PPARδ, or PGC1α can be, for example, GW6471 (N-((2S)-2-(((1Z)-1-Methyl-3-oxo-3-(4-(trifluoromethyl)phenyl)prop-1-enyl)amino)-3-(4-(2-(5-methyl-2-phenyl-1,3-oxazol-4-yl)ethoxy)phenyl)propyl) propanamide), GSK3787 (4-Chloro-N-[2-[[5-(trifluoromethyl)-2-pyridinyl]sulfonyl]ethyl]benzamide), GSK0660 (3-[[[2-Methoxy-4-(phenylamino)phenyl]amino] sulfonyl]-2-thiophenecarboxylic acid methyl ester), or another suitable compound.

In another embodiment, the compound that inhibits a component of the S6K1, mTOR, mTORC1, or upstream or downstream pathway components of S6K1 or mTORC1 mTORC1-S6K1 pathway is administered in association with a compound that is an inverse agonist of PPARα, PPARδ, or PGC1α. An inverse agonist represses activity of its target, for example, by recruiting transcriptional repression activity to PPAR binding sites. In this way, an inverse agonist serves a similar inhibitory function as an antagonist of a PPAR. In a specific embodiment, the compound is an inverse agonist of PPARδ, a well-recognized mediator of fatty acid oxidation. In a more specific embodiment, the inverse agonist is ST247.

As used herein, the term "antagonist" refers to an agent that binds to its target without activating that target, while also reducing the accessibility of the target for binding to agonists. The term "agonist," as used herein, refers to an agent that binds to and induces the activity of its target. The term "inverse agonist," as used herein, refers to an agent that binds and actively represses the activity of its target. Antagonists and inverse agonist are alike in function, in that both classes of agents act as inhibitors to prevent the activation of the target. In one embodiment, an inhibitor of a component of the mTORC1-S6K1 pathway is administered with an inhibitor of fatty acid oxidation via interaction with a PPAR receptor, such as PPARδ, wherein the inhibitor is an antagonist or an inverse agonist of PPARδ. In a very specific embodiment, the inhibitor of a component of the mTORC1-S6K1 pathway is rapamycin and the inhibitor of fatty acid oxidation is ST247.

Administration

The administration of the compound that inhibits a component of the mTORC1-S6K1 pathway can be concurrent with administration of the inhibitor of PPARα, PPARδ, or PGC1α, before administration of the inhibitor of PPARα, PPARδ, or PGC1α, or after administration of the inhibitor of PPARα, PPARδ, or PGC1α. In other words, the compounds can be administered concurrently or separately, depending on the particular embodiment.

Each of the compounds may be administered in an amount sufficient to treat the patient. The amount of active ingredient, or the therapeutic amount, that may be combined with carrier materials to produce a single dosage form will vary depending on the host treated, the particular treatment, and the particular mode of administration. Moreover, the specific dose level for each patient will depend upon a variety of factors, including but not limited to, the activity of the compound(s) employed, the age of the patient, the body weight of the patient, the general health of the patient, the sex of the patient, the diet of the patient, the time of administration, the rate of excretion, combinations of drugs administered to the patient, and the severity of the disease being treated.

When a compound that inhibits a component of the mTORC1-S6K1 pathway is administered in association with an inhibitor of PPARα, PPARδ, or PGC1α, the compounds may be administered by any suitable means. One skilled in the art will appreciate that many suitable methods of administering the compounds to an animal, and in particular, to a human, are available. Although more than one route may be used to administer a particular compound, a particular route of administration can provide a more immediate and more effective reaction than another route.

The compound that inhibits a component of the mTORC1-S6K1 pathway and the inhibitor of PPARα, PPARδ, or PGC1α can be formulated for administration by any suitable route. For example, the compounds can be in the form of tablets, capsules, suspensions, emulsions, solutions, injectables, suppositories, sprays, aerosols, and other suitable forms.

In various embodiments, a composition can include a compound that inhibits a component of the mTORC1-S6K1 pathway, an inhibitor of PPARα, PPARδ, or PGC1α, and a carrier. The carrier can be selected depending on the other compounds in the composition and the administration route for which the composition is intended.

The following Examples further illustrate particular embodiments. The specific embodiments described herein are illustrative in nature only, and are not intended to be limiting of the claimed compositions, methods or articles. Additional embodiments and variations within the scope of the claimed invention will be apparent to those of ordinary skill in the art in view of the present disclosure.

EXAMPLES

Example 1: BCR-ABL Activation of Glycolysis Through S6K1

Glycolysis was measured in IL-3-dependent FL5.12 immortalized murine hematopoietic progenitor cells that were transduced with the p210 isoform of BCL-ABL. The IL-3-dependent FL5.12 cells were cultured as described in Tandon et al., (2011) *Proc Natl Acad Sci* 108:2361-5, the disclosure of which is incorporated by reference in its entirety. Human BCR-ABL$^+$ cell lines were cultured in RPMI containing 20% FBS, HEPES, 2-ME, penicillin and streptomycin. IL-3-dependent FL5.12 cells were transduced with vector control or BCR-ABL-expressing retrovirus, then cultured in the presence or absence of IL-3 for three (3) hours. The glycolytic release of $^3H_2O$ from 5-$^3$H-glucose in the absence of growth factor was measured.

Figure 2A:
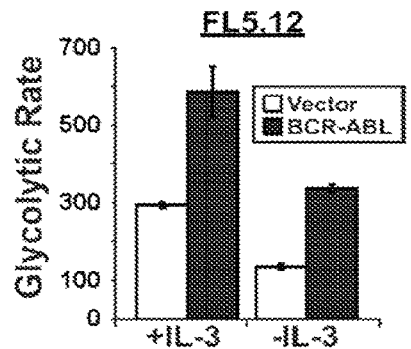
FIG. 2A illustrates the mean±standard deviation of glycolytic release of $^3H_2O$ from $^3H$-glucose in BCR-ABL$^+$ cells cultured with and without the growth factor IL-3.

To measure glycolytic release, approximately 1×10$^6$ cells were cultured with 5 μCi of 5-$^3$H-glucose for up to about 2 hours at approximately 37 degrees C. Following incubation, approximately 0.2M HCl was added to the mixture, and the mixture was transferred to an eppendorf tube inside of a closed system to separate $^3H_2O$ from $^3$H-glucose. After between approximately 24 hours and approximately 48 hours at room temperature, $^3H_2O$ was equilibrated between the inner and outer chambers and the $^3H_2O$ was measured in both chambers using a scintillation counter and standardized to controls. $^3H_2O$ was used as the standard to determine the efficacy of equilibration. BCR-ABL substantially increased glycolysis in cells cultured in either the presence or absence of cytokine (namely, IL-3), as is illustrated in FIG. 2A.

Figure 2B:
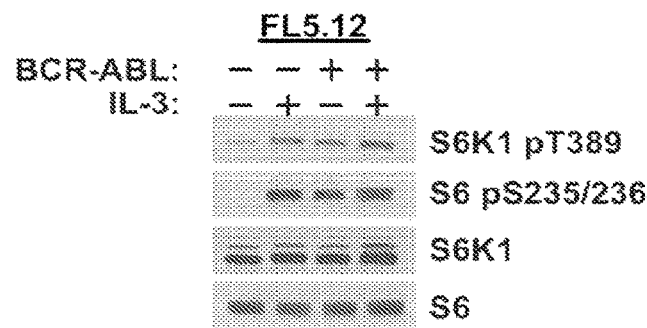
FIG. 2B shows the results of an immunoblot that demonstrate that BCR-ABL activates S6K1.

As shown in FIG. 2B, increased glycolysis was associated with cytokine-independent activation of S6K1. In particular, vector control and BCR-ABL$^+$ cells were cultured for three (3) hours in the absence of growth factor, then restimulated for thirty (30) minutes for analysis of S6K1 phosphorylation at T389 and the phosphorylation of ribosomal protein S6 at serines 235/236.

Figure 2C:
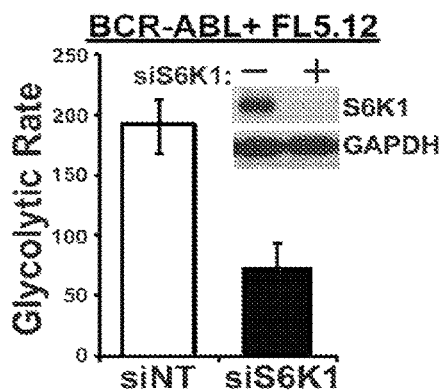
FIG. 2C illustrates the glycolytic rate in BCR-ABL$^+$ FL5.12 cells at normal and knockdown levels of S6K1.

BCR-ABL$^+$ FL5.12 cells were cultured in the absence of IL-3. Approximately lag of Accell pools of siRNA duplexes targeting S6K1 or non-targeting siRNA (Dharmacon) was used to transfect approximately 1×10$^6$BCR-ABL$^+$ FL5.12 where indicated in FIG. 2C. Transfection was completed using the G-016 program on the Nucleofactor II (Lonza). As shown in FIG. 2C, S6K1 knockdown reduced glycolysis in BCR-ABL$^+$ cells. This demonstrates that S6K1 signaling plays a role in maintaining glycolysis.

Figure 2D:
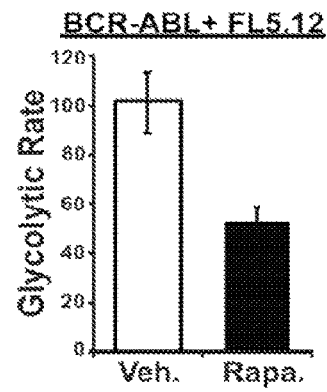
FIG. 2D illustrates the effect of rapamycin on the glycolytic rate in BCR-ABL$^+$ FL5.12 cells.
Figure 2E:
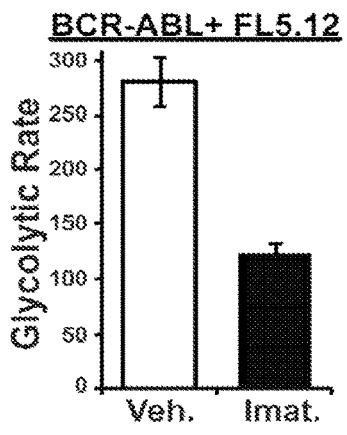
FIG. 2E illustrates the effect of imatinib on the glycolytic rate in BCR-ABL$^+$ FL5.12 cells.
Figure 2F:
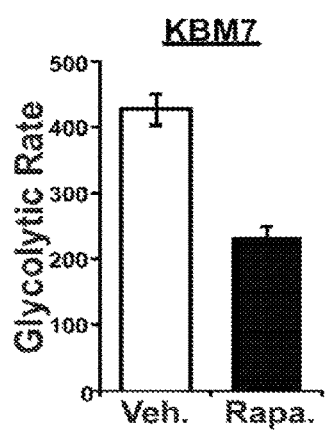
FIG. 2F illustrates the effect of rapamycin on the glycolytic rate in human BCR-ABL$^+$ KBM7 cells.
Figure 2G:
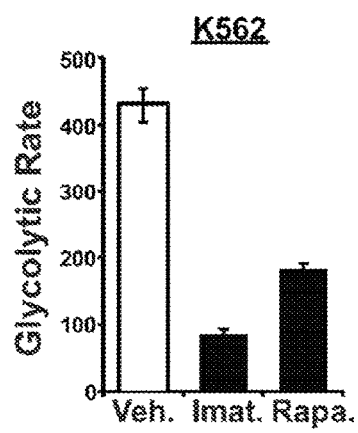
FIG. 2G illustrates the effect of rapamycin and imatinib on the glycolytic rate in human BCR-ABL$^+$ FL5.12 K562 cells.

Similar to S6K1 knockdown, rapamycin (20 nM, LC Labs) suppressed glycolysis in BCR-ABL$^+$ FL5.12 cells as well as human BCR-ABL$^+$ cell lines KBM7 and K562, as shown in FIGS. 2D, 2F, and 2G. In addition, the BCR-ABL tyrosine kinase inhibitor imatinib (1.5 μM) also reduced glycolysis, as shown in FIGS. 2E and 2G, indicating that elevated glycolysis in these cells can be induced by the transforming oncogene. Small ribosomal protein S6 (pS$^6$) phosphorylation was measured. Reduced phosphorylation of pS6 in both instances indicates that both imatinib and rapamycin reduced S6K1 activity. This demonstrates that mTORC1-S6K1 signaling mediates the induction of glycolysis downstream of BCR-ABL.

Example 2: BCR-ABL Survival is Glucose-Dependent

As shown above, BCR-ABL is a strong activator of S6K1. Accordingly, it was hypothesized that BCR-ABL$^+$ cells require glycolysis for viability. In comparison, other transforming events utilize alternative metabolic pathways to support viability, such as the requirement for autophagy by cells overexpressing Bcl-xL. See, e.g., Lum et al., (2005) *Cell* 120:237-248.

BCR-ABL$^+$ FL5.12 cells were cultured in cytokine-free medium containing either 0.2 mM glucose ("low glucose"; -Glucose) or 10 mM glucose ("high glucose", +Glucose) for 48 hours. The mean viability and standard deviation were determined by propidium iodide exclusion in a FACSAria flow cytometer (BD). Cells were washed three times in PBS and resuspended at a concentration of 2×10$^5$ per mL in media supplemented with 2 μg/mL of propidium iodide (Molecular Probes) prior to analysis. For the viability analysis of BCL-ABL$^+$ primary bone marrow cells, viability was measured after withdrawal from cytokines for five (5) days in high glucose or low glucose media. Methods used for culturing cells and measuring viability are described above and below.

Figure 3A:
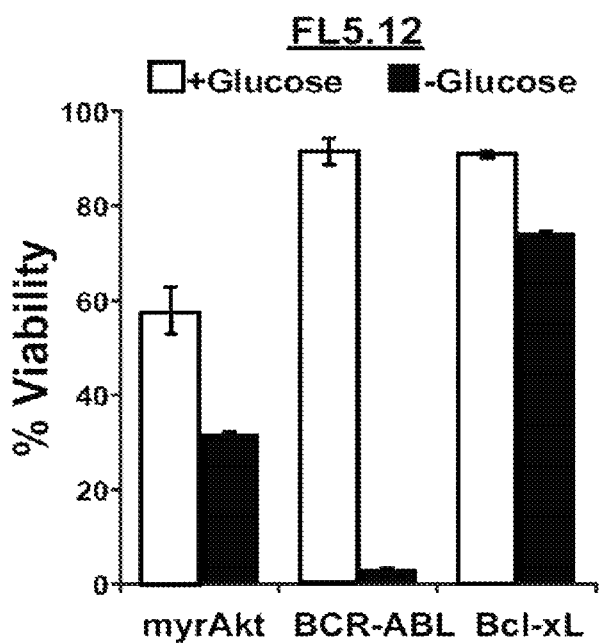
FIG. 3A illustrates the viability of myrAkt-expressing FL5.12 cells, BCR-ABL$^+$ FL5.12 cells, and Bcl-xL-expressing FL5.12 cells in 10 mM glucose (+glucose) and 0.2 mM glucose (−glucose) media.
Figure 3B:
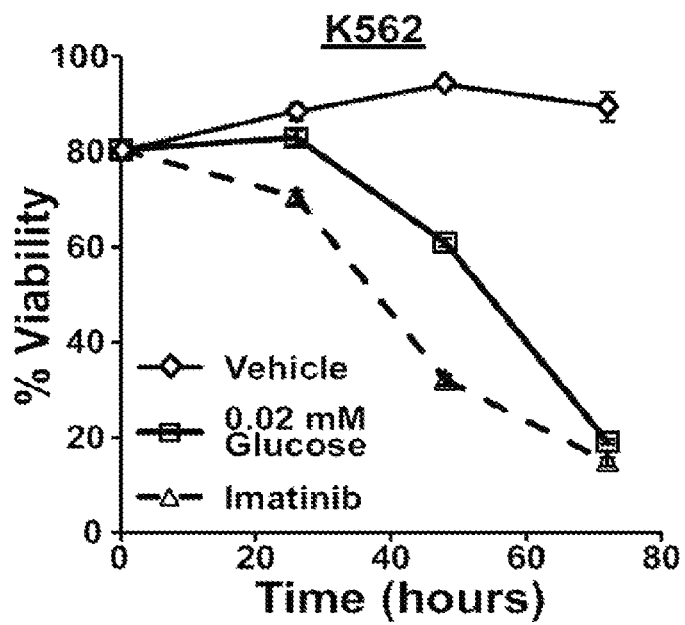
FIG. 3B illustrates the viability of BCR-ABL$^+$ K562 cells in 0.2 mM glucose and imatinib-treated media.

The viability of cells cultured in low glucose medium was significantly reduced compared to cells cultured in high glucose medium, as shown in FIG. 3A. In addition, the cell death of BCR-ABL$^+$ cells exceeded that of cells expressing constitutively active myristoylated Akt (myrAkt), a recognized mediator of glucose-dependent survival. See, e.g., Plas et al., (2001) *J Biol Chem* 276:12041-8 and Rathmell et al., (2003) *Mol Cell Biol* 23:7315-28. In contrast, Bcl-xL-dependent survival, which depends more on autophagy than glycolysis for survival, exhibited minor cytotoxicity in response to reduced glucose availability, and is also shown in FIG. 3A for reference. This demonstrates that BCR-ABL-activated survival is glucose-dependent.

Example 3: S6K1 is Not Required for the BCR-ABL Survival Program

As shown above, S6K1 inactivation suppresses glycolysis and BCR-ABL-activated survival is glucose-dependent.

Accordingly, it was hypothesized that S6K1 inactivation would trigger cell death in BCR-ABL$^+$ cells.

Viability of BCR-ABL$^+$ FL5.12 cells treated with the siRNA pool targeting S6K1 and of BCR-ABL$^+$ FL5.12 cells treated with the non-targeting siRNA pool was measured and compared to viability of myrAkt$^+$ FL5.12 cells treated with the siRNA pool targeting S6K1 or the non-targeting siRNA pool. Methods for measuring the viability of the cells, transfection, and cell culturing are described above and below. The results are shown in FIG. 4A. Though loss of S6K1 was sufficient to reduce survival in glucose-dependent cells expressing an activated form of Akt (myrAkt$^+$ FL5.12 cells), the loss of S6K1 did not trigger cell death in BCR-ABL$^+$ cells. FIG. 4B illustrates the efficacy of S6K1 knockdown in both the BCR-ABL$^+$ cells and the myrAkt$^+$ cells used for the viability analysis in FIG. 4A.

To understand how the inactivation of S6K1 reduced glycolysis without triggering cell death in BCR-ABL$^+$ cells, the requirement for glucose in cells transfected with control and S6K1 siRNAs was determined. Methods for transfection are described above and below. In vector control cells, the presence or absence of S6K1 had no impact on the ability of cells to survive in the presence or absence of glucose, as shown in FIG. 4C. In BCR-ABL$^+$ cells, survival was compromised in low glucose conditions, as shown in FIG. 3A. As shown in FIG. 4C, after knockdown of S6K1, BCR-ABL$^+$ cells acquired a survival advantage, sustaining an increase in viability in low glucose media.

To confirm the survival advantage of BCR-ABL$^+$ cells after S6K1 knockdown, an shRNA hairpin targeting S6K1 with a targeting sequence independent of the sequences used for siS6K1 experiments reduced S6K1 expression in BCR-ABL$^+$ FL5.12 cells, as shown in FIG. 4D. In addition to reducing S6K1 expression, the knockdown conferred a survival advantage when the cells were cultured in low glucose media.

ATP levels of S6K1-knockdown cells and control were measured at a time point prior to commitment to apoptosis. The time point was a time point prior to cleavage of Caspase 3. As shown in FIG. 4E, the S6K1-knockdown cells sustained higher levels of ATP compared to control cells. This suggests that BCR-ABL$^+$ cells activate a metabolic pathway that can confer a bioenergetics advantage.

Rapamycin triggers S6K1 inactivation by preventing its phosphorylation by mTORC1. In BCR-ABL$^+$ FL5.12 cells, rapamycin did not induce cell death in glucose-containing media, and conferred a survival advantage under low glucose conditions, as shown in FIG. 4F. Rapamycin also enhanced survival in BCR-ABL$^+$ primary mouse hematopoietic cells cultured under low glucose conditions, as shown in FIG. 4G. In the human K562 line, rapamycin also enhanced cell survival under low glucose conditions (FIG. 4H). This demonstrates that inactivation of mTORC1-S6K1 permits BCR-ABL$^+$ cells to induce a glucose-independent survival program that can at least partially substitute for the survival signals transduced by S6K1.

Under nutrient starvation conditions, mTORC1-S6K1 signaling can be acutely extinguished. See, e.g., Inoki et al., (2003) *Cell* 115:577-90; Kim et al., (2008) *Nat Cell Biol* 10:935-45; Nobukuni et al., (2005) *Proc Natl Acad Sci USA* 102: 14238-43; and Sancak et al., (2008) *Science* 320: 1496-501. S6K1 phosphorylation and the phosphorylation of the ribosomal protein S6 were examined over time after switching cells to low-glucose conditions to determine relative activity of S6K1 downstream of BCR-ABL under nutrient limiting conditions. BCR-ABL$^+$ FL5.12 cells were cultured in the absence of cytokine and in low glucose media for the indicated times prior to lysis. Methods utilized for cell culture are described above and below. Phosphorylation was analyzed by immunoblot. S6K1 and S6 phosphorylation was elevated at the time points examined, relative to control cells. S6K1 signaling was attenuated, but detectable, at early time points. S6K1 and S6 phosphorylation exhibited a modest recovery at later time points. This indicates that downstream of BCR-ABL, S6K1 signaling can continue to regulate metabolism and survival under nutrient-limiting conditions.

Figure 5A:
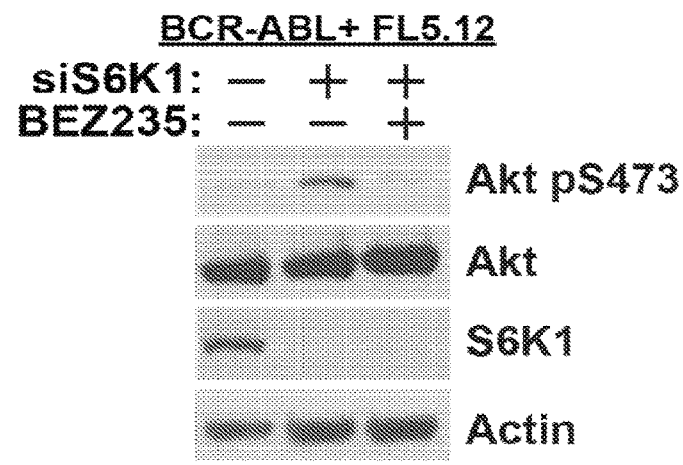
FIG. 5A depicts an immunoblot illustrating rebound activation of Akt phosphorylation triggered by S6K1 knockdown, which was inhibited by the PI3K inhibitor BEZ235.
Figure 5B:
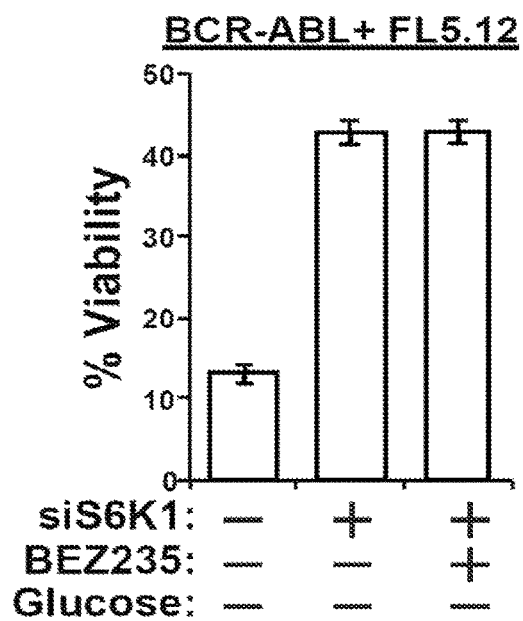
FIG. 5B illustrates that the survival advantage triggered by S6K1 knockdown was not abrogated by addition of BEZ235.

Although Akt activation has been previously associated with glucose-dependent survival (see FIG. 4A), rebound activation of Akt was tested for association with increased survival in BCR-ABL$^+$ cells cultured under low glucose conditions. As shown in FIG. 5A, in BCR-ABL$^+$ FL5.12 cells, S6K1 knockdown triggered increased Akt phosphorylation at serine 473. This indicates that rebound activation of Akt is associated with increased survival in BCR-ABL$^+$ cells cultured under low glucose conditions. Inactivation of mTORC1 and S6K1 can trigger increases in the activity of Akt and other upstream kinases, due to knockdown or loss of feedback regulation. The PI3K inhibitor BEZ235 (LC Labs) prevented the increase in Akt activation, as shown in FIG. 5A, but did not prevent glucose-independent survival in response to S6K1 inactivation, as shown in FIG. 5B.

Figure 5C:
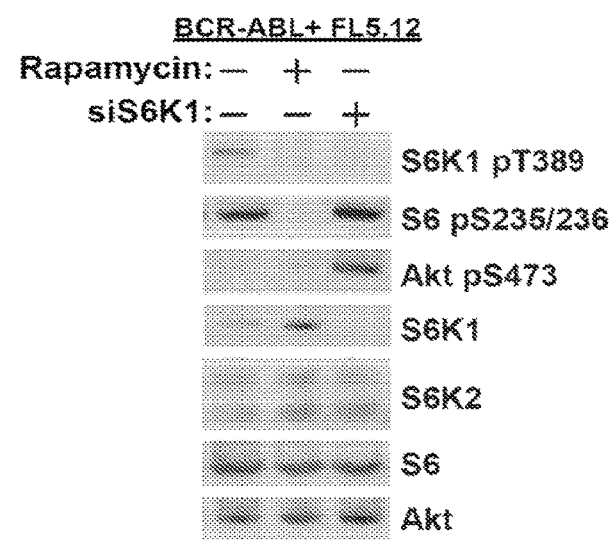
FIG. 5C depicts an immunoblot illustrating rebound activation of Akt was not sustained in cultures treated with rapamycin overnight.

Rapamycin treatment can induce rebound Akt activation in short-term cultures, but long term treatment can suppress Akt activation by the upstream kinase mTORC2. See, e.g., Sarbassov, et al., (2006) *Mol Cell* 22:159-68. Rapamycin did not trigger increased Akt phosphorylation, despite sustained glucose-independent survival in cultures treated with rapamycin overnight, as shown in FIGS. 5C and 4F. In addition, although S6K2 has been shown to functionally compensate for S6K1 inactivation in cellular transformation, there was no observed alteration in S6K2 expression levels in response to S6K1 knockdown or rapamycin, as shown in FIG. 5C. This indicates that rebound activation of Akt is not required for glucose-independent survival.

Example 4: S6K1 is not Required for BCR-ABL Leukemogenesis

Chemotherapeutic treatment with rapamycin can interfere with signaling downstream of PI3K/Akt by preventing mTORC1 phosphorylation of substrates. In mice transplanted with BCR-ABL$^+$ bone marrow cells, rapamycin can delay the development of fatal myeloproliferative disease. See, e.g., Mohi et al., (2004) *Proc Natl Acad Sci USA* 101:3130-5. Thus, there are benefits of interfering with mTORC1 signaling downstream of BCR-ABL with rapamycin. To determine the consequences of S6K1 inactivation in BCR-ABL$^+$ myeloproliferative disease, BCR-ABL$^+$ S6K1$^{+/+}$ or BCR-ABL$^+$ S6K1$^{-/-}$ bone marrow cells were transplanted into recipient mice. Lineage negative, Sca1+, cKit+(LSK) hematopoietic cells from S6K1+/+ or S6K1-/- mice (G. Thomas and S. Kozma, University of Cincinnati) were isolated using a FACSAria cell sorter. LSK cells were transduced with BCR-ABL-GFP retrovirus. Recipient C57/B16 mice (Jackson Laboratories) were lethally irradiated and approximately 10,000 GFP+ LSK cells supplemented with approximately 300,000 whole bone marrow cells were injected via the tail vein. Survival of recipient mice that exhibited symptoms of a lethal myeloproliferative disease was measured from the day of the bone marrow transplant. A log-rank test was used to determine significance. The log-rank test was performed in GraphPad Prism software, although other suitable software can be utilized.

Figure 6A:
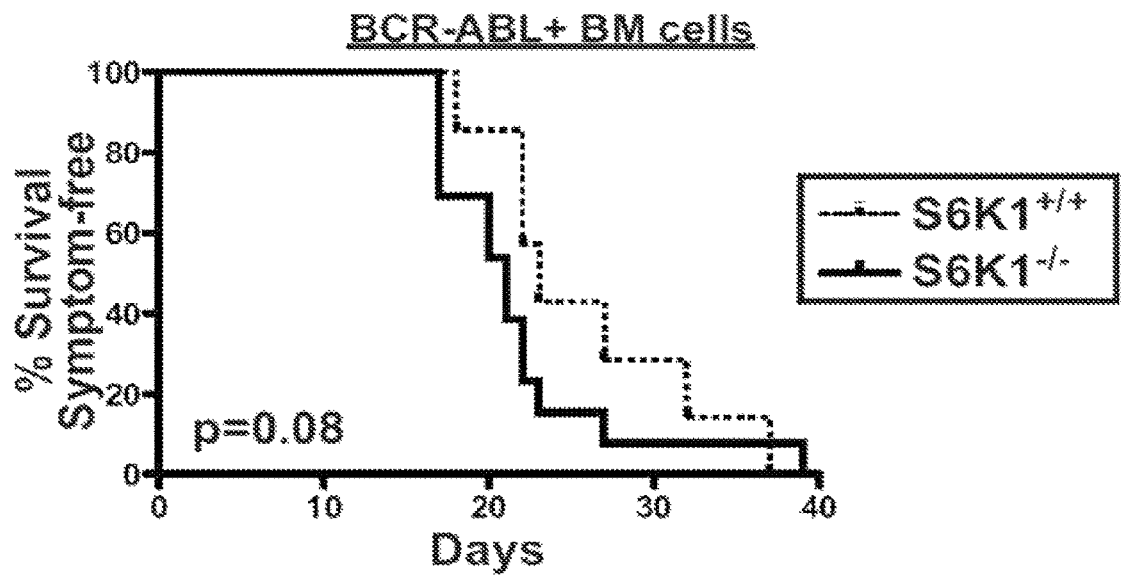
FIG. 6A is a graph illustrating the symptom-free survival of bone marrow cells from S6K1$^{+/+}$ or S6K1$^{-/-}$ mice transduced with BCR-ABL.
Figure 6B:
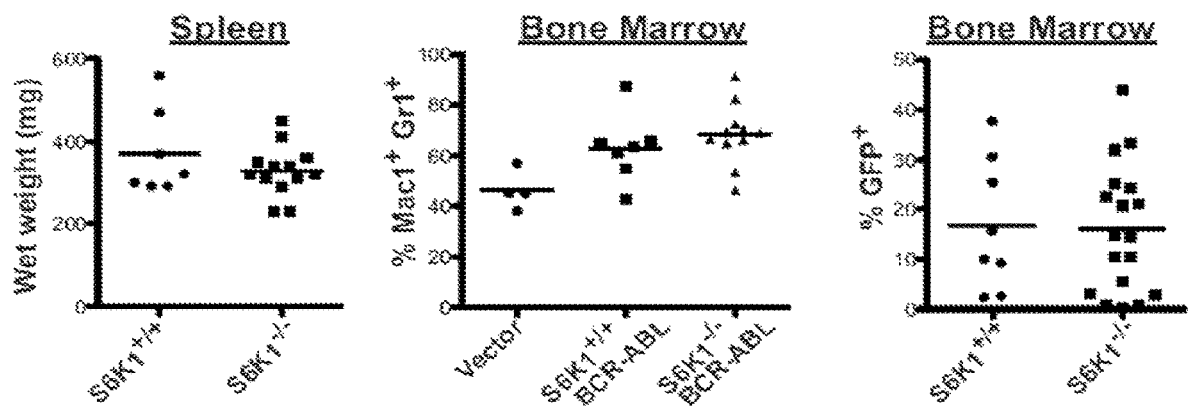
FIG. 6B illustrates the disease characteristics in mice that received the transformed cells in FIG. 6A. Shown are spleen wet weight (left), frequency of myeloid cells in the spleen (center), and frequency of BCR-ABL$^+$ (GFP$^+$) cells in the bone marrow (right) at the time of harvest.

As shown in FIG. 6A, a trend towards a more aggressive disease in mice transplanted with BCR-ABL$^+$ S6K1$^{-/-}$ bone marrow cells compared to mice transplanted with BCR-ABL$^+$ S6K1 was observed. Despite the acceleration of disease kinetics, as shown in FIG. 6B, there were no significant differences in disease characteristics at the end point of the experiment, including splenomegaly, accumulation of myeloid cells and accumulation of GFP$^+$ (BCR-ABC$^+$) cells in the bone marrow. Thus, the loss of S6K1 did not slow the progression of myeloproliferative disease, which suggested that an alternative metabolic program substituted to support BCR-ABL oncogenesis despite decreased glycolysis in S6K1-deficient cells. This demonstrates that metabolic programs can substitute for glycolysis in transformed cells.

Example 5: Loss of S6K1 Activates Fatty Acid Oxidation and Glucose-Independent Survival in BCR-ABL$^+$ Cells Activation of fatty acid oxidation (FAO) can substitute for decreased glycolysis to promote cell survival. For example, inactivation of mTORC1 can trigger a switch from glycolytic to oxidative forms of metabolism in immortalized fibroblast cells. Accordingly, the rate of FAO in BCR-ABL$^+$ cells was measured to determine if the rate of FAO responded to S6K1 knockdown.

The rate of $^3$H release from $^3$H-palmitate was used to measure FAO. The $^3$H-palmitate was adopted from Djouadi, et al., (2003) *Mol Genet Metab* 78:112-8. Between approximately 0.5×10$^6$ and approximately 1.0×10$^6$ cells were washed with PBS, then cultured with approximately 400 µL of (9,10-$^3$H) palmitate:albumin for approximately 4 hours at approximately 37 degrees C. After incubation, approximately 10% TCA was added to each tube and centrifuged at approximately 3300 rpm for approximately 10 min at approximately 4 degrees C. before being mixed with 6N NaOH and applied to ion-exchange columns. Each column was washed with approximately 1 mL of water and the eluates were counted using a scintillation counter.

As shown in FIGS. 7A, 7B, 7C, and 7D, the rate of FAO was significantly increased in both human and murine BCR-ABL$^+$ cells upon knockdown of S6K1 or upon treatment with rapamycin. Treatment with etomoxir (Sigma Aldrich), an inhibitor of the mitochondrial carnitine palmitoyl transferase (CPT) system that is essential for FAO, reduced $^3$H release, as shown in FIGS. 7A-C. Thus, the release of $^3$H from palmitate was mediated by mitochondrial FAO.

Figure 8A:
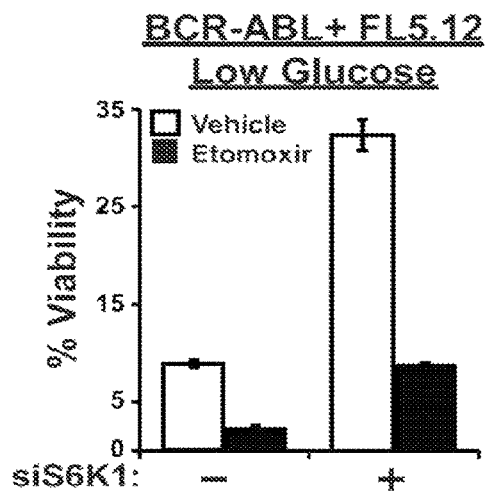
FIG. 8A illustrates the effect of etomoxir on the S6K1-knockdown survival advantage in BCR-ABL$^+$ FL5.12 cells.

To determine if FAO mediated glucose-independent survival, S6K1 knockdown BCR-ABL$^+$ cells were cultured in low glucose and in the presence and absence of etomoxir. As shown in FIG. 8A, etomoxir prevented the survival of 56K1-deficient cells, restoring glucose-dependence to BCR-ABL$^+$ cells despite the reduction in S6K1.

Figure 8B:
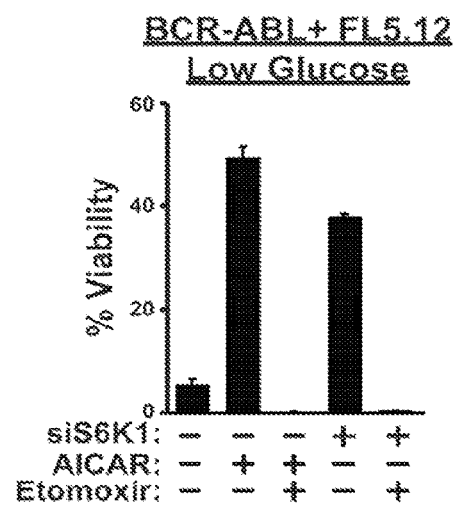
FIG. 8B illustrates the effect of etomoxir on the survival advantage in response to either AICAR or S6K1-knockdown.

Cells were cultured with 5-aminoimidazole-4-carboxamide 1-β-D-ribofuranoside (AICAR) (Cell Signaling Technology), an agonist for the AMP-activated protein kinase (AMPK), an activator of FAO, to test whether activation of FAO is sufficient for glucose-independent survival of BCR-ABL$^+$ cells. AMPK activation triggered glucose-independent survival to a level similar to the level of glucose-independent survival triggered by S6K1 knockdown, as shown in FIG. 8B. As shown in FIG. 8B, treatment with the FAO inhibitor etomoxir prevented cell survival mediated by both AICAR and S6K1 knockdown. The ability of AICAR to promote survival in an etomoxir-sensitive manner demonstrates that FAO is necessary and sufficient for glucose-independent survival in BCR-ABL$^+$ cells.

Figure 8C:
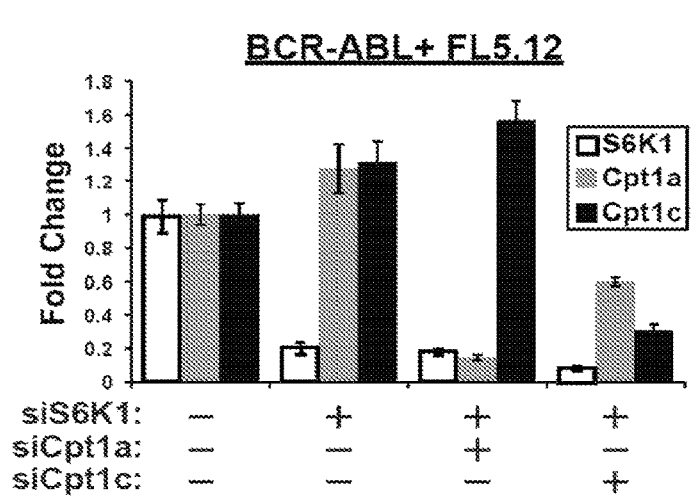
FIG. 8C illustrates the mRNA levels in response to Cpt1a-knockdown and Cpt1c-knockdown.
Figure 8D:
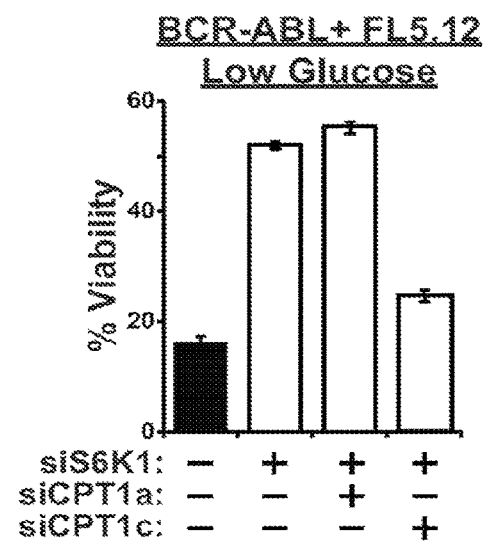
FIG. 8D illustrates the effects of Cpt1a-knockdown and Cpt1c-knockdown on glucose-independent survival in S6K1-knockdown cells.

Accordingly, the effect of depleting Cpt1a or Cpt1c on glucose-independent survival in BCR-ABL$^+$ cells lacking S6K1 was investigated. Cells were transfected with non-targeting (NT), siS6K1, siCpt1a (1a), or siCpt1c (1c), as indicated in FIG. 8C. mRNA levels were then quantified by qRT-PCR. In particular, RNA was isolated using Qiagen RNeasy mini kit. Approximately 1 µg of RNA was reverse transcribed using TaqMan Reverse Transcription reagents (Applied Biosystems). Quantitative PCR was performed using TaqMan Gene Expression Master Mix and S6K1 and Actin TaqMan proves (Applied Biosystems). Actin mRNA was used as a reference control. Cell viability was measured after 48 hours of culture in low glucose cytokine-free medium. As shown in FIGS. 8C and 8D, knockdown of Cpt1c reduced the survival of S6K1-deficient cells in low glucose conditions. However, the knockdown of Cpt1a did not reduce the survival of BCR-ABL$^+$ cells lacking S6K1. This indicates that the requirement for Cpt1c is specific to the Cpt1c isoform. The reduced viability of cells transfected with siCpt1c demonstrates that FAO is required for S6K1-independent survival.

Figure 9A:
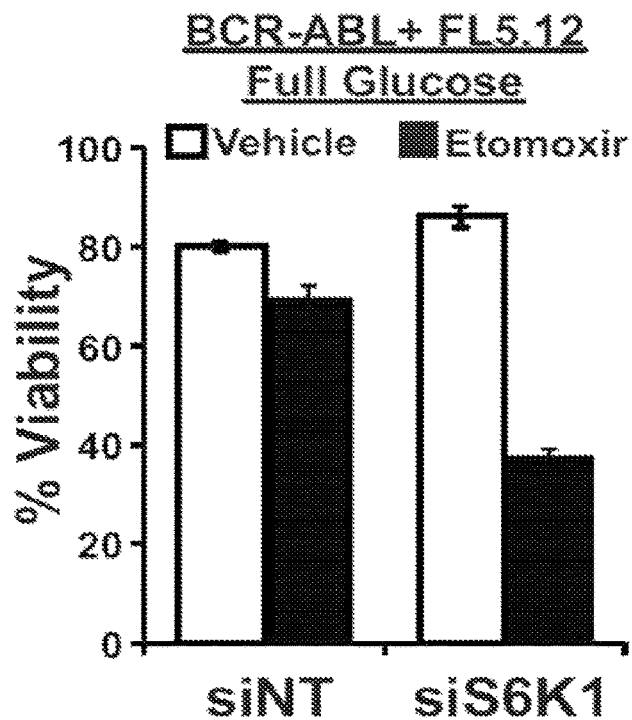
FIG. 9A illustrates the cytotoxicity of etomoxir or S6K1 knockdown in BCR-ABL$^+$ FL5.12 cells cultured in full glucose media.
Figure 9B:
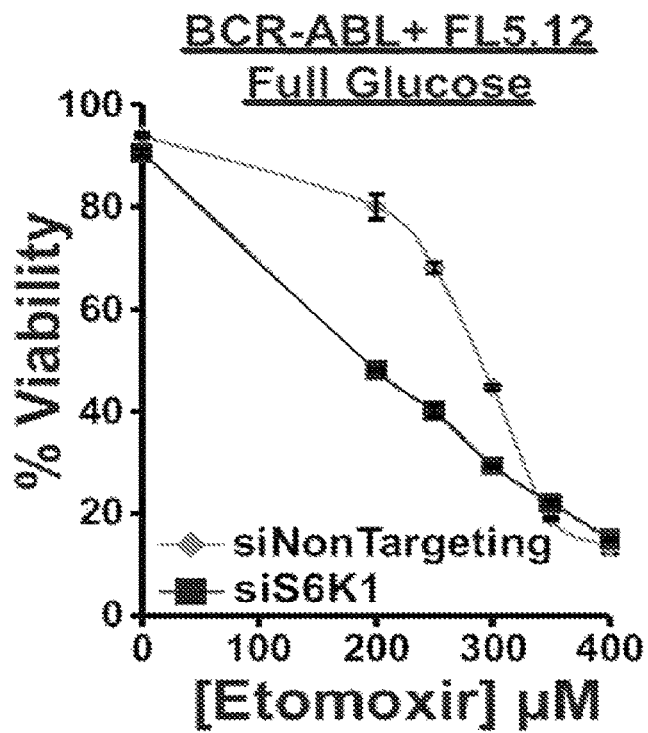
FIG. 9B illustrates the enhanced sensitivity of etomoxir in the presence of siS6K1 in BCR-ABL$^+$ FL5.12 cells cultured in full glucose media.
Figure 10:
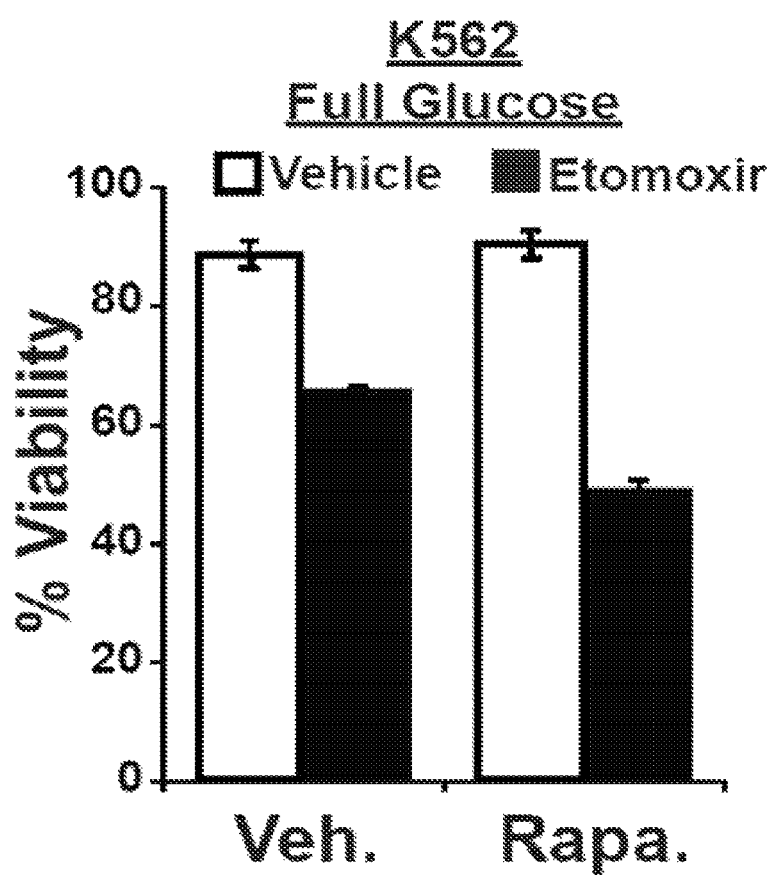
FIG. 10 illustrates the enhanced cytotoxicity of etomoxir in the presence of rapamycin in K562 cells cultured in full glucose.

The combination of siS6K1 with etomoxir was tested under full glucose conditions. S6K1 knockdown was combined with 200 µM etomoxir and used to treat BCR-ABL$^+$ FL5.12 cells. Viability of the cells was measured at approximately 48 hours. As shown in FIG. 9A, siS6K1 did not induce cell death as a single agent, while etomoxir triggered a mild cytotoxic effect as a single agent. However, the combination of S6K1 knockdown in combination with etomoxir induced significant apoptosis in cells cultured in full glucose, as shown in FIG. 9A. A similar effect was observed in rapamycin-treated cells, as shown in FIG. 10. However, the combination of rapamycin with etomoxir was not as strong as the combination of S6K1 knockdown with etomoxir. A dose curve analysis was performed, illustrating that S6K1 knockdown enhanced cell death in response to etomoxir at doses ranging from about 200 µM to about 300 µM, as shown in FIG. 9B. This demonstrates a synergistic effect between S6K1 knockdown and etomoxir.

Example 6: Inhibiting PPARα, PPARδ or PGC1α can Result in Improved Cell Death in Response to S6K1-Inactivation Since FAO is necessary and sufficient for glucose-independent survival in BCR-ABL$^+$ cells, pathways downstream of S6K1 that regulate FAO may provide additional targets that may provide a synergistic effect. In particular, the PPARα, PPARδ or PGC1α pathways may be explored.

The PPAR/PGC transcriptional complex and the AMP-activated protein kinase (AMPK) are regulators of FAO. The PPARα and PPARδ transcription factors activate FAO by recruiting PGC1α to FAO enzyme promoter sites.

Figure 11:
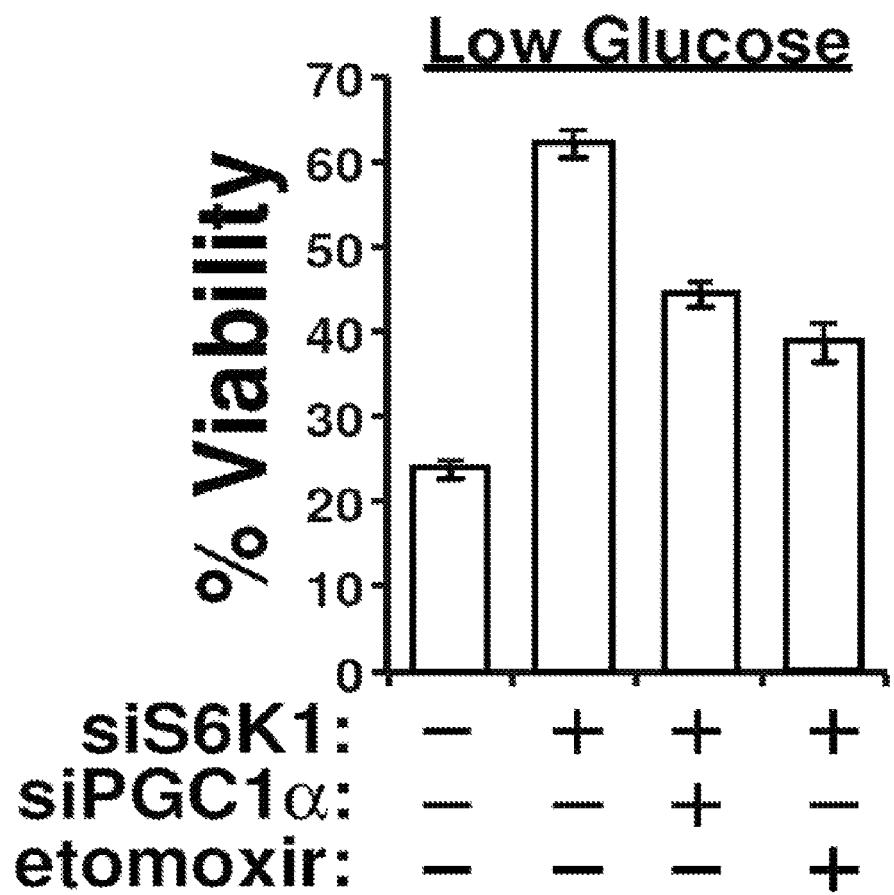
FIG. 11 illustrates the enhanced cytotoxicity of S6K1 knockdown in the presence of siPGC1a in BCR-ABL$^+$ FL5.12 cells cultured in low glucose media.

Cells are transfected with siS6K1 and/or siPGC1α according to methods explained in detail above. The cells are cultured in low glucose media for 48 hours, and viability is measured as described above. The results are shown in FIG. 11. siRNA directed against PGC1α reduces or even prevents glucose-independent survival similar to the FAO inhibitor etomoxir.

PPARα and PPARδ are explored using expression analysis, RNAi knockdown, and over expression in the cell lines used above. In addition, agonists and antagonists for PPARα and PPARδ are tested for synergistic effect with inhibitors of the mTOR pathway. Tests to determine the rate of FAO, viability of cells in low-glucose media, and transcriptional regulation will be conducted similar to those described above, using agonists and antagonists for PPARα and PPARδ in place of etomoxir. Genetic analysis of the requirement for PPARα and PPARδ indicate that inactivation of either of these mediators is sufficient to prevent glucose-independent survival.

The examples provided above, together demonstrate that S6K1-inactivation triggers the compensatory activation of FAO, a pro-survival metabolic program that was not previously available to cells expressing S6K1. The examples further demonstrate that counteracting FAO, and inhibiting for PPARα, PPARδ and PGC1α in particular, can result in improved cell death in response to S6K1-inactivation. Thus, inactivation of the pro-glycolytic signaling pathway in conduction with the inactivation of a metabolic adaptive response can be used to trigger cell death.

Example 7: Inhibition of Fatty Acid Oxidation Via PPARδ Inhibitor ST247

Figure 12:
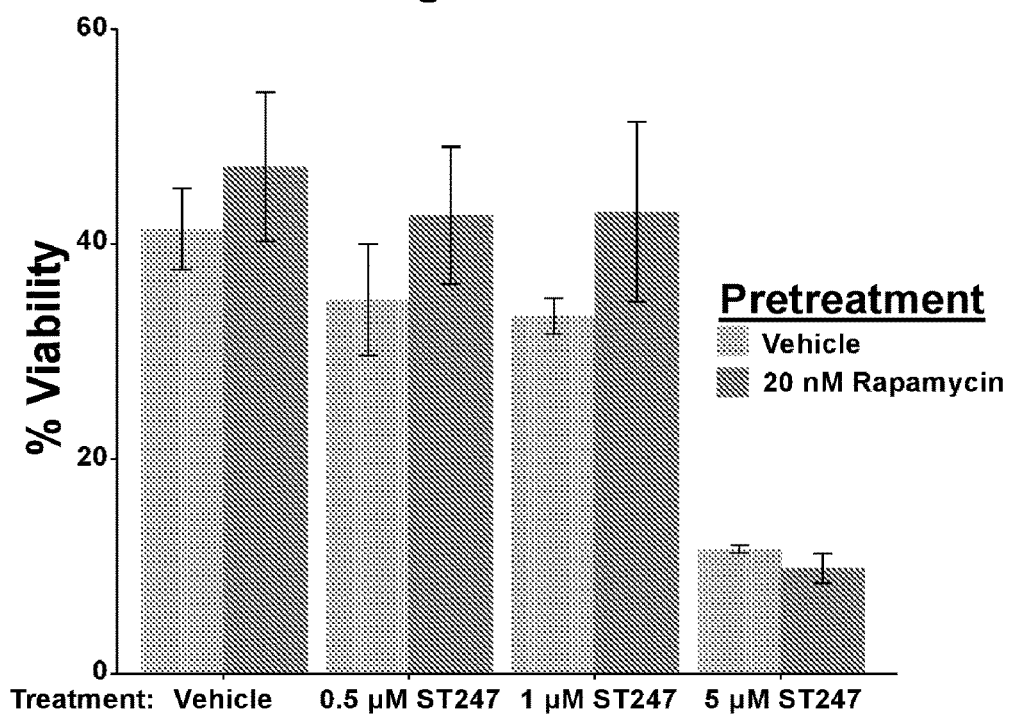
FIG. 12 illustrates the cytotoxic effect of ST247 on rapamycin-treated BCR-ABL$^+$ FL5.12 cells cultured in the absence of glucose.

Fatty acid oxidation inhibition via ST247, an inverse agonist that inhibits PPARδ activity, was examined. BCR-ABL-expressing FL5.12 cells were pretreated with vehicle control or 20 nM rapamycin overnight. Cells were cultured for 22 hours in complete medium lacking IL-3 and glucose, supplemented with the indicated treatments (vehicle, 0.5 µM ST247, 1 µM ST247, or 5 µM ST247). Viability was measured in three technical replicates by propidium iodide (PI) exclusion using a flow cytometer. Addition of 5 µM ST247 in rapamycin-treated BCR-ABL+ FL5.12 cells cultured in the absence of glucose triggered substantial cell death, as shown in FIG. 12. The effect was dose dependent, with lesser concentrations resulting in little effect in rapamycin-treated cells. Results indicate that 5 µM ST247 effectively induces cytotoxicity in glucose-starved cells.

Example 8: Effect of ST247 on Metabolic Switch to Fatty Acid Oxidation as Glycolysis Declines In order to investigate the metabolic switch as glycolysis declines, BCR-ABL-expressing FL5.12 cells were pretreated with vehicle control or 20 nM rapamycin overnight. Cells were then cultured in complete medium lacking IL-3 with 100 µM glucose (a limiting concentration) for 46 hours, supplemented with either vehicle control or 5 µM ST247. Viability was measured in three technical replicates by PI exclusion in a flow cytometer.

Figure 13:
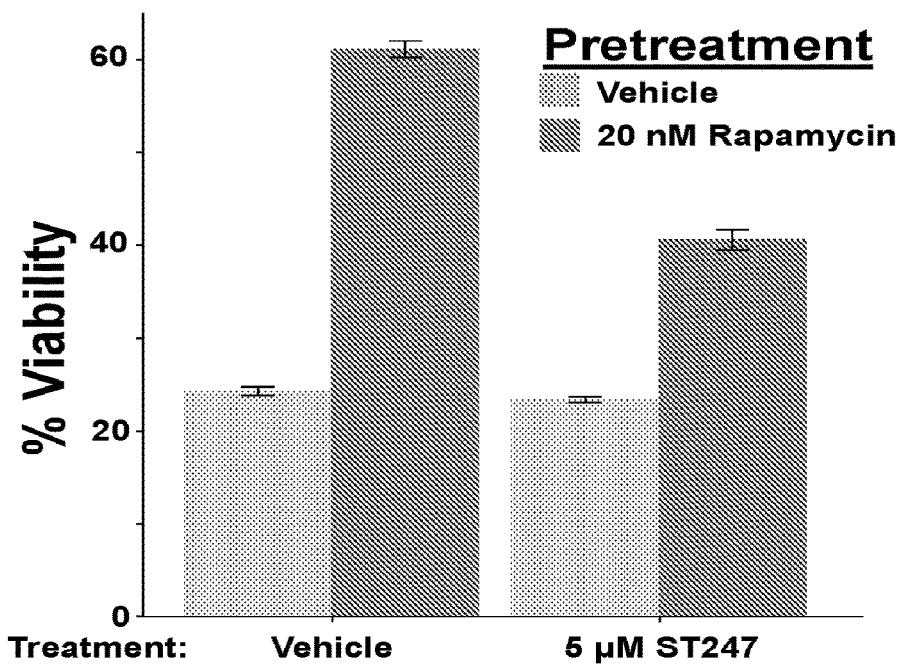
FIG. 13 illustrates the effect of ST247 on rapamycin-treated BCR-ABL$^+$ FL5.12 cells cultured in low glucose media (100 µM).

As illustrated in FIG. 13, results show that cells pretreated with 20 nM rapamycin were resistant to apoptosis under glucose-limiting conditions, compared to vehicle control-treated cells. This indicates the activation of FAO as an alternative carbon source to support cell survival. 5 µM ST247 counteracted the survival advantage induced by rapamycin, indicating that ST247 combats the metabolic switch to FAO as glucose becomes limiting.

Example 9: Effects of ST247, PPARα Antagonist GW6471, and PPARα/γ/δ Agonist GW7647 on Restoring Apoptosis in Rapamycin-Treated BCR-ABL+ Cells BCR-ABL-expressing FL5.12 cells were pretreated with vehicle control or 20 nM rapamycin overnight. Cells were then cultured in complete medium lacking IL-3 with 50 µM glucose for 48 hours, supplemented with the indicated treatments (vehicle, 1 µM GW6471, 10 µM GW7647, or 5 µM ST247). Viability was measured in three technical replicates by PI exclusion in a flow cytometer.

Figure 14:
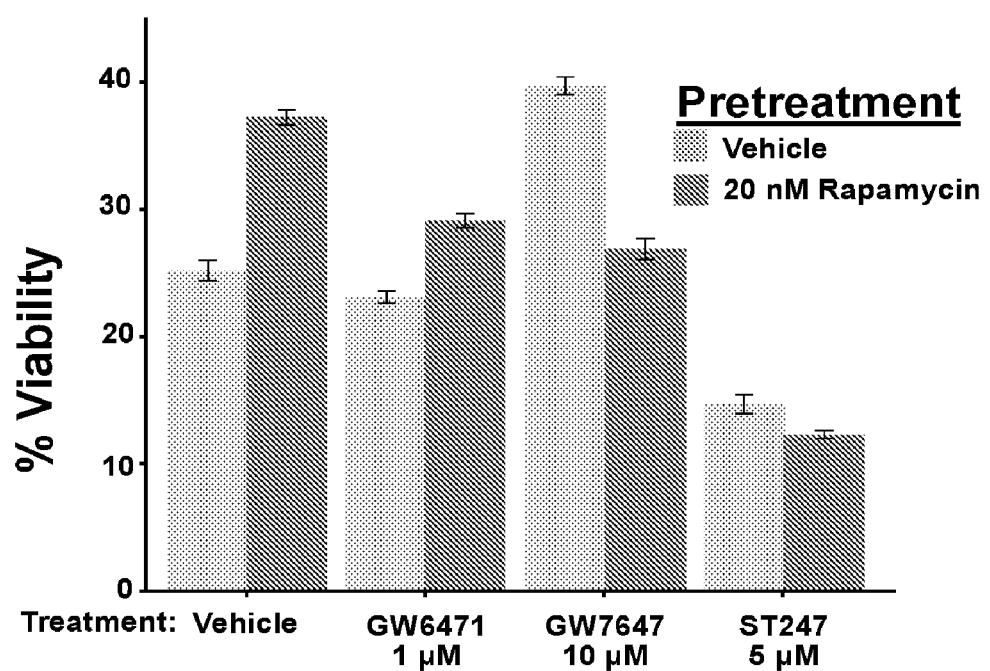
FIG. 14 illustrates the effects of inverse agonist ST247, antagonist GW6471, and agonist GW7647 on restoring apoptosis in rapamycin-treated BCR-ABL$^+$ cells in 50 µM glucose.

As illustrated in FIG. 14, results show that PPARα antagonist GW6471 was somewhat effective in restoring apoptosis. PPARα/γ/δ agonist GW7647 induced an undesired increase in viability in vehicle-control treated cells. ST247 successfully overcame the metabolic switch induced by rapamycin, thereby restoring apoptosis in rapamycin-treated BCR-ABL+ cells. Results indicate that ST247 is useful in combination with mTORC1/S6K1-inhibiting rapamycin or rapalog therapy for BCR-ABL transformed cells.

Comparison with examples 7-9 indicates that inhibition of PPARδ using the compound ST247 can be substituted for general inhibition of fatty acid oxidation by etomoxir, demonstrating a new approach for combination inactivation of PPARδ and mTORC1/S6K1 inhibition for therapy of BCR-ABL+ leukemia. The combination of ST247 with rapamycin therapy demonstrates a new method of antagonizing PPARδ function during rapamycin therapy to induce cancer cell apoptosis.

CONCLUSION

Although the example implementations have been described in language specific to structural features and/or methodological acts, it is to be understood that the implementations defined in the appended claims is not necessarily limited to the specific features or acts described. Rather, the specific features and acts are disclosed as example forms of implementing the claimed features.

What is claimed is:

1. A method of treating a subject suffering from chronic myelogenous leukemia (CML), the method consisting of administering to the subject a combination therapy consisting essentially of:
   a therapeutically effective amount of at least one compound that inhibits mTOR selected from the group consisting of rapamycin, everolimus, temsirolimus, Torin1, and BEZ235; and
   a therapeutically effective amount of at least one inhibitor of PPARα, PPARδ, or PGC1α, wherein said inhibitor of PPARα, PPARδ, or PGC1α is an antagonist or an inverse agonist of PPARα, PPARδ, or PGC1α, and wherein said inhibitor is selected from the group consisting of GW6471, GSK3787, GSK0660, and ST237.

2. The method of claim 1, wherein the at least one compound that inhibits mTOR comprises at least one compound that inhibits BCR-ABL.

3. The method of claim 1, wherein the at least one compound that inhibits mTOR is rapamycin.

4. The method of claim 1, wherein the at least one compound that inhibits mTOR and the at least one inhibitor of PPARα, PPARδ, or PGC1α are administered concurrently.

5. The method of claim 1, wherein the at least one compound that inhibits mTOR and the at least one inhibitor of PPARα, PPARδ, or PGC1α are administered separately.

6. The method of claim 1, wherein the at least one inhibitor of PPARα, PPARδ, or PGC1α comprises at least one inverse agonist of PPARδ.

7. The method of claim 6, wherein the at least one compound that inhibits mTOR and the at least one inverse agonist of PPARδ are administered concurrently.

8. The method of claim 6, wherein the at least one compound that inhibits mTOR and the at least one inverse agonist of PPARδ are administered separately.

9. A method of treating a subject suffering from chronic myelogenous leukemia, the method consisting of administering to the subject a combination therapy consisting essentially of:
   a therapeutically effective amount of an inhibitor of mTOR selected from the group consisting of rapamycin, everolimus, temsirolimus, Torin 1, and BEZ235, and a therapeutically effective amount of ST247.

10. The method of claim 9, wherein the inhibitor of mTOR is rapamycin.

* * * * *

UNITED STATES PATENT AND TRADEMARK OFFICE
CERTIFICATE OF CORRECTION

PATENT NO. : 10,835,519 B2
APPLICATION NO. : 15/851891
DATED : November 17, 2020
INVENTOR(S) : Plas et al.

Page 1 of 1

It is certified that error appears in the above-identified patent and that said Letters Patent is hereby corrected as shown below:

In the Specification

Column 1, Line 19, under the heading "GOVERNMENT INTERESTS" insert the following:
--This invention was made with government support under CA133164 and CA168815 awarded by National Institutes of Health. The government has certain rights in the invention.--

Signed and Sealed this
Nineteenth Day of January, 2021

Andrei Iancu
*Director of the United States Patent and Trademark Office*